United States Patent [19]

Hoffmann et al.

[11] 4,056,545

[45] Nov. 1, 1977

[54] MANUFACTURE OF OLEFINICALLY UNSATURATED ESTERS

[75] Inventors: Werner Hoffmann, Neuhofen; Manfred Baumann, Mannheim, both of Germany

[73] Assignee: BASF Aktiengesellschaft, Ludwigshafen, Germany

[21] Appl. No.: 705,280

[22] Filed: July 14, 1976

[30] Foreign Application Priority Data

Aug. 5, 1975 Germany .............................. 2534859

[51] Int. Cl.² .......................... C09F 5/08; C09F 7/10; C11C 3/00
[52] U.S. Cl. .............................. 260/410; 260/410.9 R; 560/210; 560/212
[58] Field of Search ...................... 260/410.9 R, 405.6, 260/405.5, 486 R, 491, 494, 410.9 E, 410.9 M, 410

[56] References Cited

U.S. PATENT DOCUMENTS 3,692,851  9/1972  Henrick et al. ............... 260/410.9 R

OTHER PUBLICATIONS

Schlosser, M. et al., "Mechanisms and Stereochemistry of the Wittig Reaction", Annalen der Chemie, 708 (1967) pp. 1–35.

Primary Examiner—Winston A. Douglas
Assistant Examiner—John F. Niebling
Attorney, Agent, or Firm—Keil, Thompson & Shurtleff

[57] ABSTRACT

A process for the manufacture of $\alpha,\beta,\gamma,\delta$-unsaturated esters containing a very high proportion of the 4(Z)-isomer, which are valuable perfume and flavor materials. The $\alpha,\beta,\gamma,\delta$-unsaturated esters are manufactured by a Wittig synthesis from phosphoranes and fumaraldehyde-acid esters under specific conditions.

8 Claims, No Drawings

MANUFACTURE OF OLEFINICALLY UNSATURATED ESTERS

The present invention relates to a process for the manufacture of α,β,γ,δ-unsaturated esters containing a very high proportion of the 4(Z)-isomer, by a Wittig synthesis from phosphoranes and fumaraldehyde-acid esters under specific conditions.

The majority of the esters manufactured with the aid of the new process possess interesting scents and flavors. A high proportion of 4(Z)-isomers is a precondition for good olfactory properties of the products (with regard to Z-E-isomerism, cf., eg., Hans Beyer "Lehrbuch der organ. Chemie," 17th edition, S. Hirzel Verlag, Stuttgart, page 66).

German Laid-Open Application DOS 2,163,868 has already disclosed a process for the manufacture of α,β,γ,δ-unsaturated carbonyl compounds by reaction of α,β-unsaturated carbonyl compounds with an organometallic compound which contains a transition metal, eg. Cu(I), a monovalent cation, eg. Li+ or [Mg-halogen]+ and an alkenyl radical.

Further, Helv. Chim. Acta, 56, Issue 3 (1973), No. 117, pages 1,176 et seq. discloses a process for the manufacture of a particular α,β,γ,δ-unsaturated ester, namely ethyl 2,4-decadienoate (also known as "pear ester") by reaction of 4,5-epoxy-2-trans-pentenal with the ylide of n-hexyltriphenylphosphonium bromide, treatment of the resulting mixture of isomeric epoxides with periodic acid and conversion of the resulting isomeric aldehydes with NaCN/MnO₂ into the corresponding mixture of ester isomers.

Both processes are very laborious and expensive in respect of the starting materials required, and the way in which the process is carried out, and can presumably not be realized industrially.

It is an object of the present invention to provide a process by means of which it is possible to manufacture, simply and economically, α,β,γ,δ-unsaturated esters having interesting olfactory properties, especially ethyl 2,4-deca-dienoate containing a high proportion of the 4(Z)-isomer.

We have found, surprisingly, that this object is achieved and that 2(E), 4(Z)-unsaturated esters of the general formula I

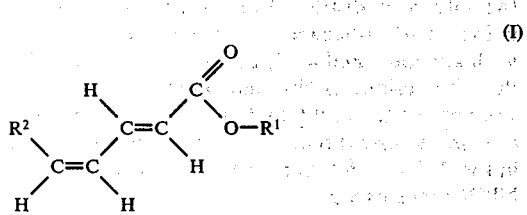

where R¹ is a saturated hydrocarbon radical of 1 to 4 carbon atoms, preferably ethyl, and R² is a linear or branched hydrocarbon radical of 1 to 10 carbon atoms, preferably a saturated hydrocarbon radical of 1 to 7 carbon atoms, which contain a high proportion of 4(Z) isomers, are obtained when the solution of a phosphorane of the formula II $$R^2 - CH = P(R^3)_3 \qquad (II)$$

where R² has the above menings and R³ is phenyl or toluyl, in an ether solvent, is introduced at from 60° to 150° C into a solution of a fumaraldehyde-acid ester of the formula III

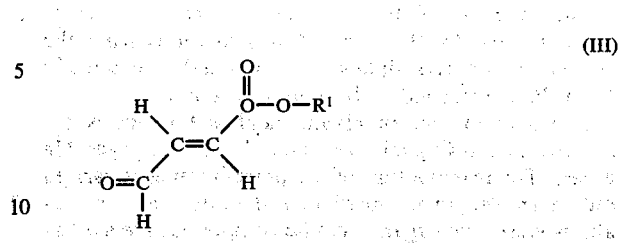

where R¹ has the abovementioned meanings, in an ether solvent; the reaction mixture may then be left at from 60° to 150° C for a period of not more than about 30 minutes and then worked up by conventional methods.

Under the reaction conditions according to the invention, the desired esters are obtained in yields of from 60 to 70% of theory. The proportion of 4(Z) constituent in the isomer mixture is about 85%, as a result of which the esters can be used as valuable perfume and flavor materials.

In contrast, carrying out the reaction of the phosphoranes of the formula II with a fumaraldehyde-acid ester under the conventional conditions of the Wittig reaction proved unsuccessful. The desired esters were merely obtained in yields of from about 5 to 13% of theory (see Comparative Example 8). Presumably, under these conditions, the activated ester group in the fumaraldehydeester reacted as rapidly, or even more rapidly, than the aldehyde group. Bohlmann and Inhoffen (Chem. Ber. 89 (1956), 1276–81) made similar observations and recommended that the difficulties should be avoided by carrying out the reaction by dropwise addition of the phosphorane to the carbonyl compound. However, even this process variant did not result in a significant increase in the yield of the reaction of the phosphoranes of the formula II with the fumaraldehyde-esters.

To achieve the desired 4(Z) configuration it is necessary, according to statements in the literature regarding the "cis-Wittig reaction" (M. Schlosser and K. F. Christmann, Annalen der Chemie 708 (1967), 8 et seq.) to carry out the reaction in the absence of salts, in nonpolar solvents such as benzene or heptane, and at temperatures which are kept as low as possible. Under the working conditions described in the said publication as suitable for preparative methods of cis-selective carbonyl-olefination, the desired esters of the formula I were only obtainable in very low yields from the phosphoranes of the formula II and fumaraldehyde-acid esters (see Comparative Examples 9a and 9b).

It was therefore very surprising that on reaction of the phosphoranes II with a fumaraldehyde the desired α,β,γ,δ-unsaturated esters were obtained in good yields and with a very high proportion of 4(Z) constituent in the isomer mixture by adhering to the following combination of process parameters:

1. Introduction of the phosphorane solution into the solution of the carbonyl compound.
2. The use of ether solvents.
3. The use of temperatures of from 60° to 150° C during the addition of the phosphorane solution.

If benzene or petroleum ether is used as solvent, the desired esters are obtained in yields of only from about 20 to 30%.

The fumaraldehyde-esters required for carrying out the process of the invention can be manufactured in a multi-stage reaction by photo-oxidation of furfuraldehyde.

The required solutions of the phosphoranes can be manufactured by the conventional methods from the corresponding triarylphosphonium halides, especially from the corresponding bromides or iodides.

The manufacture of alkylidenephosphoranes is described, eg., in Organic Reactions 14 (1965), pages 278 et seq. The manufacture of the phosphoranes is carried out in an anhydrous medium and under an inert gas atmosphere, and organometallic compounds are used as the requisite proton acceptors. For example, a solution of phenyl-lithium or butyl-lithium in ether can be introduced, under nitrogen, into a suspension of about 1 equivalent of the phosphonium salt in an ether solvent. The reaction is in general carried out cold and the progress of the reaction can be assessed by observing the intense color of the phosphoranes formed. However, it is also possible to manufacture the alkylidenephosphorane by slowly adding the triarylphosphonium salt to a mixture of $NaNH_2$ and an ether solvent or to a mixture of $NaNH_2$ and liquid $NH_3$, with subsequent replacement of the liquid $NH_3$ by an ether solvent.

By way of example, the manufacture of the phosphoranes by reaction of the triarylphosphonium halides with $NaNH_2$ in liquid $NH_3$ will be explained in more detail.

The alkyltriarylphosphonium halide is added slowly, at below $-35°$ C, and preferably at from about $-35°$ to $-40°$ C, under $N_2$, to a mixture of $NaNH_2$ in liquid $NH_3$. The $NaNH_2$ is used in equivalent amount to the halide, whilst the $NH_3$ also serves as the solvent and is therefore used in large excess. The reaction mixture is in general allowed to react for a further period of from about 30 to 90 minutes in the cold, whilst stirring, the $NH_3$ is then evaporated off and the residue is taken up in a dry ether solvent. The mixture is then advantageously boiled under reflux for from about 30 to 90 minutes. It is then decanted from the salt which has formed, giving an intensely colored solution of the phosphoranes in the ether.

Examples of suitable ether solvents are, above all, tetrahydrofuran (THF), glycol dimethyl ether and di-n-butyl ether. With regard to the success of the reaction, the choice is not critical, although tetrahydrofuran is preferred because it is particularly cheap and easy to separate.

To carry out the process according to the invention, the solution of the phosphorane is added slowly, under a blanket of inert gas, to the heated solution of the fumaraldehyde-acid ester. By "slowly" we mean approximately at the rate at which the phosphorane is used up. If the rate is too high, both functional groups of the fumaraldehyde-acid ester can be attacked simultaneously. The optimum rate of addition can be readily determined by preliminary experiment. In general, 0.5 to 5%, preferably 0.5 to 1.7%, by weight of the total amount of the solution of the phosphorane is run into the solution of the fumaraldehyde-acid ester per minute. The reaction temperature is from about 60° to 150° C. The reaction is advantageously carried out at the boiling point of the ether solvent.

The reaction time is in general from 15 to 60 minutes.

The reactants are in general used in about equimolar amounts. The use of a slight excess (from about 10 to 20%) of fumaraldehydeacid ester increases the yield.

The solvents used for dissolving the fumaraldehyde-acid ester are again, above all, tetrahydrofuran, glycol dimethyl ether of di-n-butyl ether.

The reaction mixture is worked up in the customary manner for Wittig reactions, eg. by distilling off the solvent, taking up the residue in a low-boiling inert solvent, and washing and distilling the solution.

Using the process according to the invention it is possible to obtain the 2(E), 4(Z)-unsaturated esters of the formula I, which can be used as good scents and aromas, from industrially readily accessible starting compounds, by a simple method which gives good yields and good steric selectivity.

EXAMPLES 1 TO 7

0.25 mole of one of the alkyltriphenylphosphonium bromides shown in the Table is added slowly, at from $-35°$ to $-40°$ C, under $N_2$, to 10 g of $NaNH_2$ in 200 ml of liquid $NH_3$.

After stirring for a further 30 minutes, the $NH_3$ is evaporated and the residue is taken up in 200 ml of the dry solvent shown in the Table. The reaction mixture is then heated for 1 hour to the boil under reflux. The salt is then allowed to sediment and the resulting brownish red solution is added dropwise, in the course of 1 hour, to a boiling solution of 36 g of fumaraldehyde-acid ethyl ester in 50 ml of the chosen solvent. The presence of salts, formed in the reaction, which may have been retained in the solution does not have an adverse effect on either the yields or the stereo-selectivity. When using tetrahydrofuran as the solvent (Examples 1 to 4 and 7), a reaction temperature of approx. 65° to 70° C results, while the use of glycol dimethyl ether (Examples 5 and 6) results in a reaction temperature of approx. 82° to 87° C. After heating for 15 minutes under reflux, the solvent is distilled off, the residue is extracted by boiling with n-hexane, the hexane solution is washed with aqueous methanol, the hexane is stripped off and the oily residue is distilled. During distillation, small amounts of fumaraldehyde-acid ethyl ester are recovered in the first runnings. The (Z)-constituent indicated in the Table is determined by gas chromatography and NMR spectroscopy.

TABLE

| Example | $R^2-CH_2-CH_2-P(C_6H_5)_3 \cdot HBr$ | Ester | Solvent | (Z)-content | boiling point/ mm Hg | Yield | Scent |
|---|---|---|---|---|---|---|---|
| 1 | $CH_3-CH_2-CH_2-P(C_6H_5)_3 \cdot HBr$ | $CH_3-CH_2-CH=CH-CH=CH-\underset{\underset{O}{\parallel}}{C}-OC_2H_5$ | tetrahydrofuran | 80-85% | 92-93/13 | 64% | fruity |
| 2 | $CH_3-(CH_2)_3-P(C_6H_5)_3 \cdot HBr$ | $CH_3-(CH_2)_2-CH=CH-CH=CH-\underset{\underset{O}{\parallel}}{C}-OC_2H_5$ | " | 84% | 53/0.05 | 73% | fruity, green |
| 3 | $\underset{CH_3}{\overset{CH_3}{>}}CH-(CH_2)_2-P(C_6H_5)_3 \cdot HBr$ | $\underset{CH_3}{\overset{CH_3}{>}}CH-CH_2-CH=CH-CH=CH-\underset{\underset{O}{\parallel}}{C}-OC_2H_5$ | " | 85% | 60-61/0.1 | 60% | green, fatty, fruity |
| 4 | $CH_3-(CH_2H_5)-P(C_6H_5)_3 \cdot HBr$ | $CH_3-(CH_2)-CH=CH-CH=CH-\underset{\underset{O}{\parallel}}{C}-OC_2H_5$ | " | 85% | 83/0.09 | 68% | very ripe pears |
| 5 | $CH_3-(CH_2)_5-P(C_6H_5)_3 \cdot HBr$ | $CH_3-(CH_2)_4-CH=CH-CH=CH-\underset{\underset{O}{\parallel}}{C}-OC_2H_5$ | glycol dimethyl ether | 85% | 83/0.09 | 62% | very ripe pears |
| 6 | $CH_3-(CH_2)_6-P(C_6H_5)_3 \cdot HBr$ | $CH_3-(CH_2)_5-CH=CH-CH=CH-\underset{\underset{O}{\parallel}}{C}-OC_2H_5$ | " | 85% | 86-87/0.2 | 60% | musky, fruity |
| 7 | $CH_3-(CH_2)_7-P(C_6H_5)_3 \cdot HBr$ | $CH_3-(CH_2)_6-CH=CH-CH=CH-\underset{\underset{O}{\parallel}}{C}-OC_2H_5$ | tetrahydrofuran | 85% | 87-88/0.01 | 57% | green, fatty, fruity |

EXAMPLE 8 (COMPARATIVE EXAMPLE)

Reaction under the conventional conditions of a Wittig olefination.

a. 107 g (0.25 mole) of triphenyl-n-hexyl-phosphonium bromide are introduced in portions into 10 g of NaNH$_2$ (0.25 mole) in 200 ml of liquid NH$_3$ at −40° C, and the reaction mixture is stirred for 60 minutes at this temperature. The NH$_3$ is then evaporated and the residue, in 200 ml of benzene, is boiled under reflux for 60 minutes.

32 g (0.25 mole) of fumaraldehyde-acid ethyl ester in 50 ml of benzene are added dropwise in the course of 45 minutes at from 0° to 5° C. The reaction mixture is stirred for 60 minutes at from 0° to 5° C and for 16 hours at 22° C. It is then filtered and the dark brown solution is concentrated.

The residue ix extracted by boiling with hexane and is washed with aqueous methanol. After concentration, 37.3 g are left.

On distillation, 6.2 g (12.6%) of the desired product, having an E,Z-content of 75%, are obtained at a boiling point of 85° C/0.02 mm Hg.

b. 107 g (0.25 mole) of triphenyl-n-hexyl-phosphonium bromide are introduced in portions into 10 g of NaNH$_2$ (0.25 mole) in 200 ml of liquid NH$_3$ at −40° C and the reaction mixture is stirred for 60 minutes at this temperature. The NH$_3$ is then evaporated and the residue, in 200 ml of tetrahydrofuran (THF) is boiled under reflux for 60 minutes. Thereafter, 32 g (0.25 mole) of fumaraldehyde-acid ethyl ester in 50 ml of THF are added dropwise in the course of 45 minutes at from 0° to 5° C. The reaction mixture is stirred for 30 minutes at 0° C and is then boiled under reflux for 2 hours. Thereafter it is filtered and the solution is concentrated. The residue is extracted by boiling with petroleum ether. 29 g of a dark oil are obtained; on distillation under reduced pressure, this gives 4.4 g (9% of theory) of the desired product, boiling at 85°–90° C/0.2 mmHg and having an E,Z-content of 75%.

EXAMPLE 9 (COMPARATIVE EXAMPLE)

Reaction under the conventional conditions for cis-olefinations (cf. M. Schlosser et al., Annalen der Chemie 708, (1967), 31–33).

a. 299 g of triphenyl-n-hexyl-phosphonium bromide are added in portions to a solution of 27.2 g (0.7 mole) of NaNH$_2$ in 400 ml of liquid NH$_3$ at −40° C. The reaction mixture is stirred for a further 60 minutes at −40° C. The NH$_3$ is then evaporated and the residue, in 400 ml of toluene, is boiled under reflux for 30 minutes. The mixture is then allowed to cool and the salt formed during the reaction is allowed to sediment.

The brownish red solution is decanted and is then added in the course of 30 minutes at 0° C into a solution of 90 g of fumaraldehyde-acid ethyl ester in 150 ml of a 1:1 (by volume) mixture of toluene and petroleum ether. The reaction mixture obtained is stirred for a further hour at 0° C. It is then filtered, the solution is concentrated and the residue is chromatographed on silica gel (neutral grade, from Merck) using an 8:2 mixture of petroleum ether/ether. 35 g of substance are eluted. On distillation, only 2.2 g of a product mixture, in which the desired compound is present, are obtained at a boiling point of 85°–100° C/0.1 mm Hg.

b. Using the method described in Example 8b), a solution of the ylene in tetrahydrofuran is prepared from 10 g of NaNH$_2$ and 107 g of triphenyl-n-hexyl-phosphonium bromide.

The colored solution obtained is decanted from the salt which has formed and is added dropwise, in the course of 30 minutes, at from 0° to 10° C to a solution of 32 g of fumaraldehyde-acid ethyl ester in 100 ml of tetrahydrofuran. The mixture is then stirred first for 1 hour at 0° C and then for 16 hours at room temperature. On working up by the method described in Example 8a), 11 g (corresponding to 20.5% of theory) of the ethyl ester of the formula I, having an E,Z-content of 80%, are obtained.

We claim:

1. A process for the manufacture of Δ,β, γ,δ-unsaturated esters containing a high proportion of the 2(E), 4(Z)-isomer of the formula:

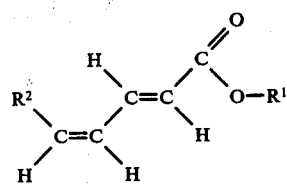

(I)

wherein R$^1$ is a saturated hydrocarbon radical of 1 to 4 carbon atoms and R$^2$ is a linear or branched hydrocarbon radical of 1 to 10 carbon atoms, which process comprises slowly introducing an ether solvent solution of a phosphorane of the formula:

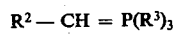

(II)

wherein R$^2$ is as defined above and R$^3$ is phenyl or tolyl, at from 60° to 150° C, into an ether solvent solution of a fumaraldehyde-acid ester of the formula:

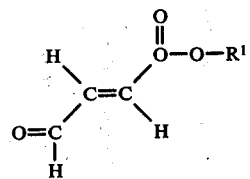

(III)

wherein R$^1$ is as defined above.

2. A process as claimed in claim 1 wherein the reaction mixture formed by introduction of the phosphorane solution is, after completion of such introduction, maintained at reaction temperature not more than 30 minutes.

3. A process as claimed in claim 1 which includes the step of adding an alkyltriarylphosphorane halide of the general formula:

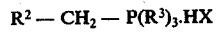

wherein R$^2$ and R$^3$ are each as defined in claim 1 and wherein X is halogen, at a temperature of less than −35° C and under an inert gas atmosphere, to a mixture of NaNH$_2$ in liquid ammonia, evaporating off the ammonia and dissolving the resulting phosphorane of formual (II) in the ether solvent.

4. A process as claimed in claim 1 wherein the ether solvent of the phosphorane solution is tetrahydrofuran, glycol dimethyl ether or di-n-butyl ether.

5. A process as claimed in claim 1 wherein the ether solvent of the ester (III) solution is tetrahydrofuran, glycol dimethyl ether or di-n-butyl ether.

6. A process as claimed in claim 1 wherein the solution of the phosphorus is added to the solution of the fumaraldehyde-acid ester substantially at the rate at which it is consumed.

7. A process as claimed in claim 1 wherein from 0.5 to 1.7% of the total amount of the solution of the phosphorane is added per minute to the solution of the fumaraldehyde-acid ester.

8. A process as claimed in claim 1 wherein the proportion of 4(Z) isomer is about 85%.

* * * * *

UNITED STATES PATENT AND TRADEMARK OFFICE
CERTIFICATE OF CORRECTION

PATENT NO. : 4,056,545
DATED : November 1, 1977
INVENTOR(S) : HOFFMANN ET AL

It is certified that error appears in the above-identified patent and that said Letters Patent are hereby corrected as shown below:

In the specification, column 2, formula (III), in the structure delete "$\overset{O}{\underset{/}{\overset{\|}{O}-}}$" and substitute --$\overset{O}{\underset{/}{\overset{\|}{C}-}}$--.

In claim 1, column 8, line 14, delete "$\Delta, \beta$" and substitute --$\mathcal{L}, \beta$--; lines 40-45, in formula (III), in the structure delete "$\overset{O}{\underset{/}{\overset{\|}{O}-}}$" and substitute --$\overset{O}{\underset{/}{\overset{\|}{C}-}}$--.

In claim 3, column 8, line 64, cancel "formual" and substitute --formula--.

Signed and Sealed this

Third Day of April 1979

[SEAL]

Attest:

RUTH C. MASON
*Attesting Officer*

DONALD W. BANNER
*Commissioner of Patents and Trademarks*